(12) United States Patent
Markel et al.

(10) Patent No.: US 7,808,227 B2
(45) Date of Patent: Oct. 5, 2010

(54) SYSTEMS AND METHODS FOR DETECTING IMPURITIES IN REACTOR SYSTEMS

(75) Inventors: Eric J. Markel, Kingwood, TX (US); Robert O. Hagerty, La Porte, TX (US); Michael E. Muhle, Kingwood, TX (US)

(73) Assignee: Univation Technologies, LLC, Houston, TX (US)

( * ) Notice: Subject to any disclaimer, the term of this patent is extended or adjusted under 35 U.S.C. 154(b) by 278 days.

(21) Appl. No.: 11/821,602

(22) Filed: Jun. 25, 2007

(65) Prior Publication Data

US 2008/0042655 A1    Feb. 21, 2008

Related U.S. Application Data

(60) Provisional application No. 60/819,326, filed on Jul. 7, 2006.

(51) Int. Cl.
*G01N 27/00* (2006.01)

(52) U.S. Cl. .................. 324/71.1; 422/131; 324/453; 526/59; 526/74; 526/82

(58) Field of Classification Search ............ 324/71.1; 526/56–60

See application file for complete search history.

(56) References Cited

U.S. PATENT DOCUMENTS

| | | | |
|---|---|---|---|
| 2,964,511 A | 12/1960 | Cottle | |
| 3,268,604 A | 8/1966 | Boyd, Jr. | |
| 3,268,605 A | 8/1966 | Boyd, Jr. | |
| 3,460,125 A | 8/1969 | Liebermann et al. | |
| 3,493,854 A | 2/1970 | Zurbrick | |
| 3,515,987 A | 6/1970 | Zurbrick et al. | |
| 3,559,049 A | 1/1971 | Liebermann et al. | |
| 3,656,339 A * | 4/1972 | Narain | 73/31.03 |
| 4,112,209 A * | 9/1978 | Gunsher et al. | 526/65 |
| 4,264,331 A | 4/1981 | Klein et al. | |
| 4,423,371 A | 12/1983 | Senturia et al. | |
| 4,433,286 A | 2/1984 | Capots et al. | |
| 4,448,943 A | 5/1984 | Golba et al. | |
| 4,532,311 A * | 7/1985 | Fulks et al. | 526/62 |
| 4,710,550 A | 12/1987 | Kranbuehl | |
| 4,723,908 A | 2/1988 | Kranbuehl | |
| 4,803,251 A * | 2/1989 | Goode et al. | 526/59 |
| 4,855,370 A | 8/1989 | Chirillo et al. | |

(Continued)

FOREIGN PATENT DOCUMENTS

DE            293592 A  *   9/1991

(Continued)

OTHER PUBLICATIONS

Vargason; Liquid Multipart System Provides Automatic Real-Time Monitoring of Wet-Process Station Liquids, *Microcontamination*, pp. 39-41 (1990).

(Continued)

Primary Examiner—Timothy J Dole
Assistant Examiner—Benjamin M Baldridge

(57) ABSTRACT

The present invention is directed to various methods and systems for detecting at least one impurity in a bulk fluid. In certain embodiments, the methods are performed in conjunction with a polymerization reactor system such as a gas-phase reactor system.

57 Claims, 8 Drawing Sheets

U.S. PATENT DOCUMENTS

| | | | |
|---|---|---|---|
| 4,888,948 A | 12/1989 | Fisher et al. | |
| 5,018,380 A | 5/1991 | Zupancic et al. | |
| 5,034,479 A | 7/1991 | Eisinger et al. | |
| 5,136,247 A | 8/1992 | Hansen | |
| 5,369,495 A | 11/1994 | Lagowski | |
| 5,714,678 A | 2/1998 | Jurcik et al. | 73/31.03 |
| 5,760,298 A | 6/1998 | Fisher et al. | 73/61.42 |
| 6,111,034 A * | 8/2000 | Goode et al. | 526/59 |
| 6,472,885 B1 | 10/2002 | Green et al. | |
| 6,548,610 B2 * | 4/2003 | Bartilucci et al. | 526/74 |
| 6,586,538 B2 * | 7/2003 | Ford et al. | 526/74 |
| 6,774,643 B2 | 8/2004 | Magill | |
| 6,831,140 B2 * | 12/2004 | Muhle et al. | 526/74 |
| 2003/0089159 A1 | 5/2003 | Roe | 73/28.04 |
| 2004/0214969 A1 * | 10/2004 | Ehrman et al. | 526/84 |
| 2005/0148742 A1 | 7/2005 | Hagerty et al. | |
| 2005/0203259 A1 * | 9/2005 | Poliafico et al. | 526/74 |
| 2006/0128908 A1 * | 6/2006 | Apecetche et al. | 526/72 |
| 2006/0160965 A1 * | 7/2006 | Goode et al. | 526/82 |

FOREIGN PATENT DOCUMENTS

| | | |
|---|---|---|
| WO | 2005/100972 | 10/2005 |

OTHER PUBLICATIONS

Translation of granted patent EP 0890834.
Translation of granted patent DE2843246.

* cited by examiner

Example showing effect of introduction of an impurity into system
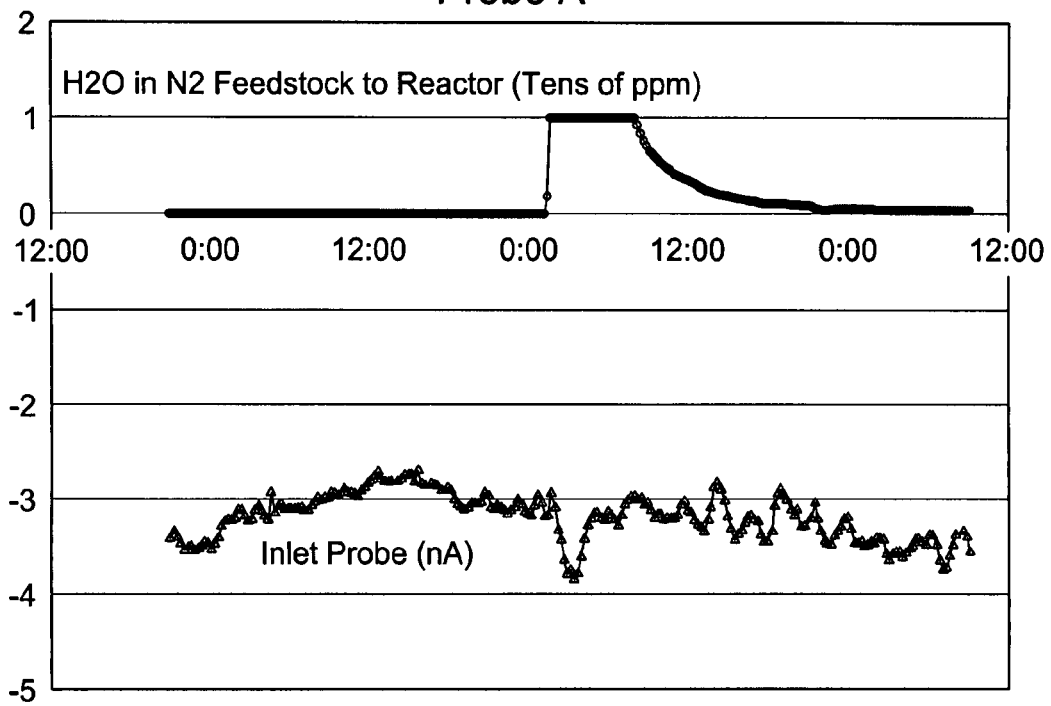
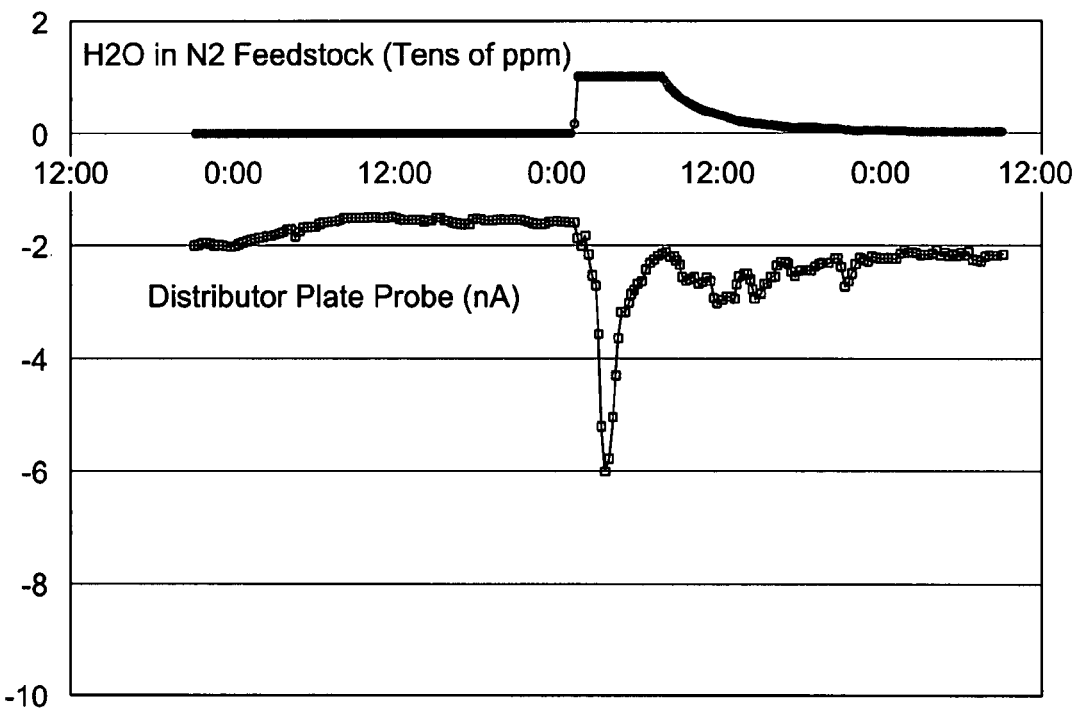
Fig. 6

SYSTEMS AND METHODS FOR DETECTING IMPURITIES IN REACTOR SYSTEMS

CROSS REFERENCE TO RELATED APPLICATIONS

This application claims the benefit of Application No. 60/819,326, filed Jul. 7, 2006, the disclosure of which is incorporated by reference.

FIELD OF THE INVENTION

The present invention relates to impurity detection, and more particularly, this invention relates to systems and methods for detecting impurities in bulk material.

BACKGROUND OF THE INVENTION

In the gas phase process for production of polyolefins such as polyethylene, a gaseous alkene (e.g., ethylene), hydrogen, co-monomer and other raw materials are converted to solid polyolefin product. Generally, gas phase reactors include a fluidized bed reactor, a compressor, and a cooler. The reaction is maintained in a two-phase fluidized bed of granular polyethylene and gaseous reactants by the fluidizing gas which is passed through a distributor plate near the bottom of the reactor vessel. The reactor vessel is normally constructed of carbon steel and rated for operation at pressures up to about 50 bars (or about 3.1 MPa). Catalyst is injected into the fluidized bed. Heat of reaction is transferred to the circulating gas stream. This gas stream is compressed and cooled in the external recycle line and then is reintroduced into the bottom of the reactor where it passes through a distributor plate. Make-up feedstreams are added to maintain the desired reactant concentrations.

Operation of most reactor systems is critically dependent upon good mixing for uniform reactor conditions, heat removal, and effective catalyst. The process must be controllable, and capable of a high production rate. Due in part to the high cost of catalyst and the need to control the rate of reaction, very small amounts of catalyst are used to affect the polymerization of ethylene and co-monomer in gas phase polyethylene production. However, small amounts of impurities in feedstock, even at sub-ppm levels, can adversely affect reactor operations by deactivating the catalyst. Impurities in gaseous feedstocks for polyethylene production typically include $H_2O$, $O_2$, CO, $CO_2$, acids, sulfur compounds and other compounds. Such impurities can impact operations by deactivating catalyst. As catalyst becomes deactivated, the production rate suffers. If high levels of impurities are present, production may cease entirely. While theoretically, the injection of more catalyst into the system would maintain production, it is not desirable to do so. Rather, it would be preferable to identify the source of even minute levels of catalyst-deactivating impurities as soon after their introduction into the reactor system as possible.

Other effects such as static generation have also been attributed to low levels of impurities. In the case of Ziegler-Natta catalysts, the impurities can react with an aluminum alkyl, used as a typical activator or cocatalyst, and form prostatic agents. Electrostatic forces are believed to be a major factor in problematic and frequent "sheeting" events. Sheeting is associated with the undesirable accumulation of polymer along the reactor wall in the zone occupied by the main fluid bed. This accumulation is believed to be associated with fine particles or "fines," the fines being less than 100-200 mesh. These fines are more influenced by static electrical forces due to their larger surface area relative to their mass, a counter-play of static versus inertial forces.

The stagnation of the resin particles results in a significant reduction in the heat transfer from the nascent particles, precisely at the point in their growth when heat generation per unit surface area is at a maximum. The next result is an interplay of forces which results in particle overheating, melting and agglomerating with adjacent particles, both overheated and normal type particles. The net result is the formation of sheets along the vessel wall. Progressive cycles in this process eventually result in the growth of the sheet and its falling into the fluid bed. These sheets interrupt fluidization, circulation of gas and withdrawal of the product from the reactor, requiring a reactor shutdown for removal.

Background references include U.S. Pat. Nos. 4,855,370, 4,888,948, 5,034,479, U.S. Patent Application Publication No. 2005/148742, and DE 10 2004 019387 (Abstract).

Accordingly, it would be desirable to detect the presence of impurities in gas phase polyolefin and other reactor systems so as to allow avoidance of the problems associated with such impurities.

SUMMARY OF THE INVENTION

The present invention is broadly directed to various methods and systems for detecting at least one impurity in a bulk fluid. In certain embodiments, the methods are performed in conjunction with a polymerization reactor system such as gas-phase reactor system. The invention is also broadly directed to various systems in which impurities are detected.

In the methods and systems of the present invention, at least one electrical probe in contact with a bulk material is monitored for determining the presence of at least one impurity. In some embodiments, the bulk material and/or impurity may include gaseous, liquid and/or solid phase components. In some embodiments, the bulk material may consist essentially of nonpolar materials, while the impurity is a polar material.

In certain embodiments for use with or including a polymerization reactor system, at least one electrical probe is positioned in a reactor vessel of the polymerization reactor system. For example, the electrical probe may be positioned above a distributor plate of the polymerization reactor system. The electrical probe may also be positioned between a feedstock inlet and a distributor plate of the polymerization reactor system, within or outside of the reactor vessel. The electrical probe may also be positioned in a recycle line of the polymerization reactor system.

In one embodiment, monitoring the electrical probe includes monitoring a voltage flow between the electrical probe and a ground. A change in the monitored voltage may be indicative of the presence of an impurity. In some embodiments, no external electrical signal is applied to the electrical probe, the voltage being generated by the electrical probe contacting the bulk material. A current flow between the electrical probe and a ground may also be monitored.

In another embodiment, monitoring the electrical probe includes detecting a voltage differential between the probe and a ground. A change in the monitored voltage level may be indicative of the presence of at least one impurity.

In one embodiment, a second electrical probe may be monitored, and its output (or derivative thereof) compared to the output (or derivative thereof) of the first electrical probe.

The present invention is also broadly directed to various methods for determining a source of at least one impurity in a moving bulk material.

In an embodiment, a source of an impurity in a moving bulk material is determined. At least one electrical probe is placed in contact with a moving bulk material. The electrical probe is monitored. Based on a monitored response of the electrical probe, the presence of at least one impurity can be determined. A flow rate of one or more feed streams are altered, e.g., increased, reduced, or stopped, and a determination is made as to whether the altering of the flow rate of the feed stream affects the determination of whether an impurity is present. The flow rates of multiple feed streams may be altered sequentially, concurrently, etc.

In yet another embodiment, a source of at least one impurity in a moving bulk material is determined by contacting at least one electrical probe with a moving bulk material, monitoring the electrical probe, and determining presence of an impurity based on the monitoring as above. However, a source of at least one feed stream is changed. A determination is made as to whether changing the source of the at least one feed stream affects the determination of whether at least one impurity is present. The sources of multiple feed streams may be altered sequentially, concurrently, etc.

In various embodiments, the at least one electrical probe is also useable for determining a level of static electricity of solids in the bulk material.

Other aspects and advantages of the present invention will become apparent from the following detailed description, which, when taken in conjunction with the drawings, illustrate by way of example the principles of the invention.

BRIEF DESCRIPTION OF THE DRAWINGS

FIG. 6 is a chart reflecting the effect of introduction of an impurity on electrical probes.

The inventors have surprisingly found that the presence of impurities in gaseous-phase feed streams and process streams can be detected at a ppm level, and in some embodiments, preferably, at a sub-ppm level, by analyzing the signal generated by a static probe (electric probe). Sub-ppm level refers to any level on a magnitude less than one part in a million, regardless of how well that level can quantified. A change in the level of impurities is detected as a change in the amperage or voltage of the probe. This result was unexpected.

While the present invention is applicable to gas phase polyolefin production, the broad concepts and teachings herein also have applicability to many types of processes, including but not limited to, gas phase, gas/solid phase, liquid/solid phase, gas/liquid phase, and gas/liquid/solid phase reactor systems including polymerization reactor systems; gas phase, gas/solid phase, liquid/solid phase, gas/liquid phase, and gas/liquid/solid phase mass transfer systems; gas phase, gas/solid phase, liquid/solid phase, gas/liquid phase, and gas/liquid/solid phase mixing systems; gas phase, gas/solid phase, liquid/solid phase, gas/liquid phase, and gas/liquid/solid phase heating or cooling systems; gas/solid phase and gas/solid/liquid phase drying systems; etc.

For ease of understanding of the reader, as well as to place the various embodiments of the invention in a context, much of the following description shall be presented in terms of a commercial, gas phase polyethylene reactor system. It should be kept in mind that this is done by way of non-limiting examples only.

Figure 1:
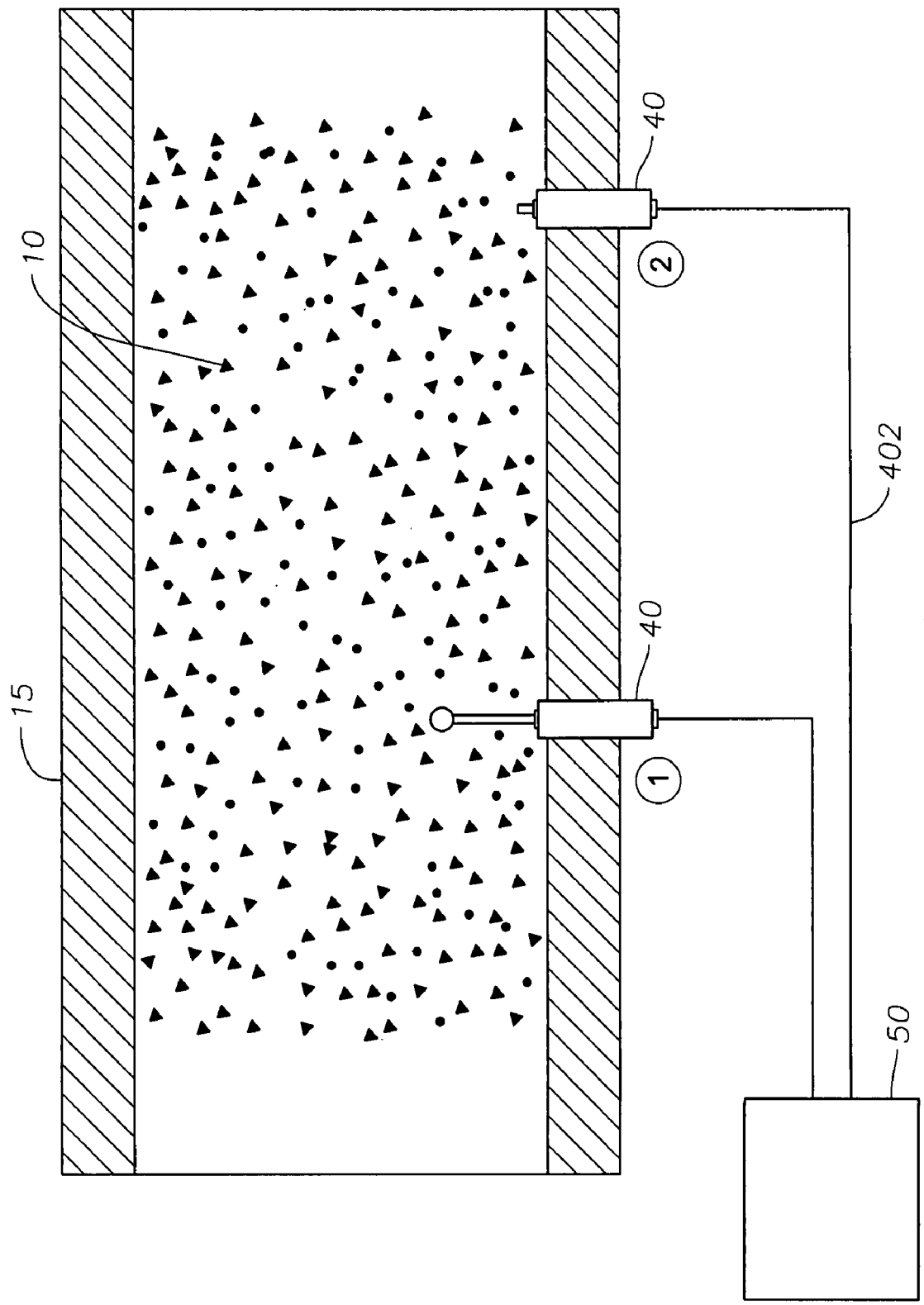
FIG. 1 is a schematic representation of the general methods, systems and/or apparatus of certain embodiments of the invention.

A general method of the invention can be described, for example, with reference to FIG. 1, in which a bulk material 10 is bounded by a barrier 15 such as a vessel. Such bulk material can be gaseous, liquid and/or solid material. In a reactor system, illustrative bulk materials may include one or more of reaction raw materials such as feedstocks, reaction products such as polymer particles, reaction adjuncts such as catalysts, reaction byproducts, etc., and other materials. Thus, the bulk material may include substantially pure individual materials as well as combinations of materials, the material(s) being present in one or more phases. One or more electrical probes (designated generally collectively using the reference numeral "40," with multiple electrical probes designated more specifically in the various figures as electrical probes with circled numbers 1, 2, 3, etc. and in the associated text herein as 40-1, 40-2, 40-3, etc.) are placed in contact with the bulk material. The response of the electrical probe 40 is monitored by processing unit 50 for determining presence of an impurity in the bulk material.

Figure 2:
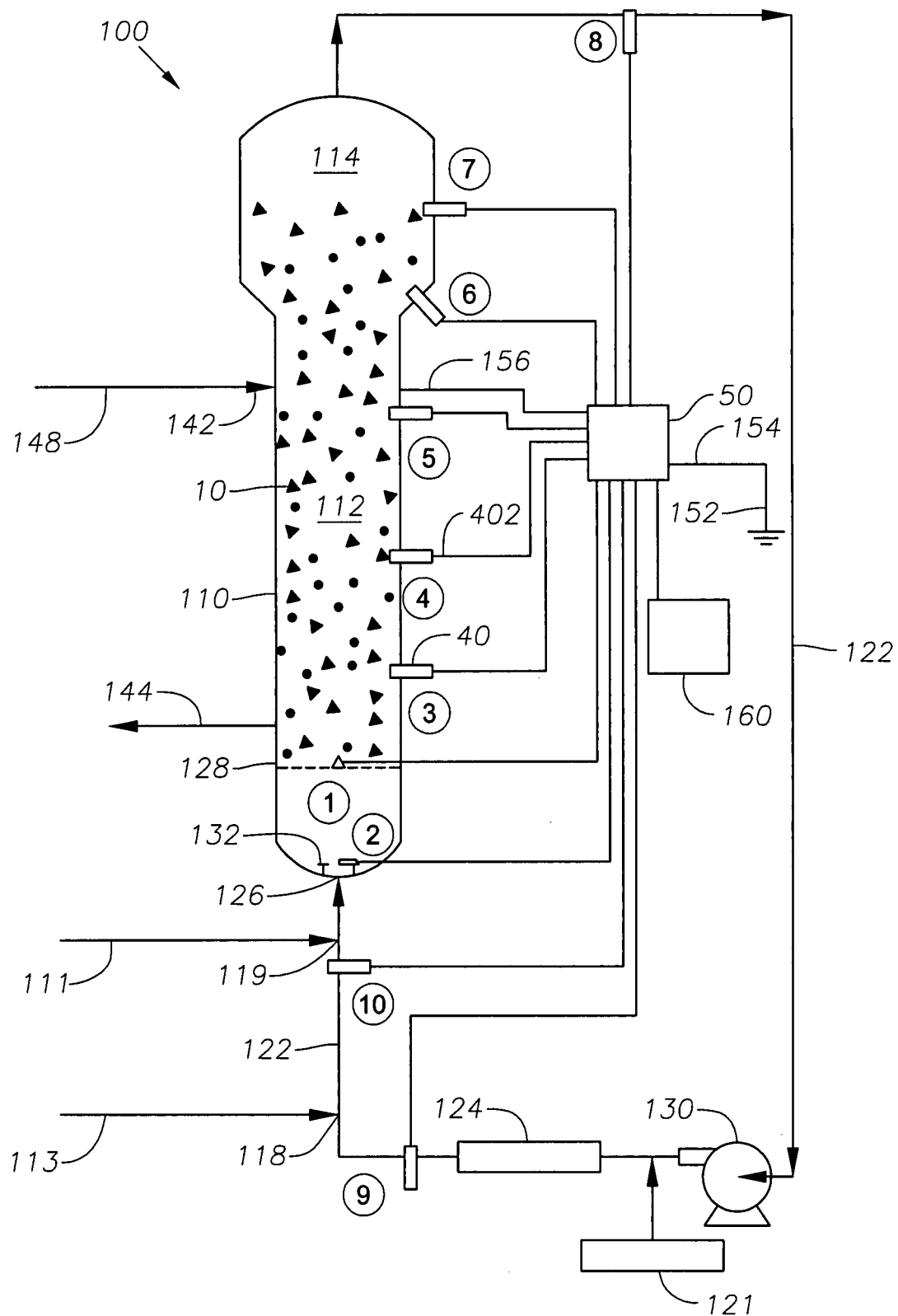
FIG. 2 is a schematic representation of the general methods, systems and/or apparatus of certain embodiments of the invention illustrating implementation in a fluidized bed polymerization reactor.

In a further generally preferred approach of the general method, with reference to FIG. 2, bulk material 10 in a fluidized bed polymerization reactor system 100 are monitored for purposes of detecting impurities in the bulk material 10. According to the general method, a gaseous monomer is added to the fluidized bed polymerization reactor vessel 110 of the reactor system 100 thereby forming polymer particles 10 in a gas phase polymerization reaction in the fluidized bed polymerization reactor vessel 110. An electrical probe 40-1 is contacted with the polymer particles in the reactor system. The electrical probe is monitored. The monitoring may include measuring the a voltage or amperage of the probe relative to a reference, e.g., a local ground 152, the reactor vessel 110 or equipment structure, etc. Based on a monitored response of the electrical probe, the presence of an impurity can be determined. Electrical probes 40 can be placed in many different positions in the reactor system 100 besides the reactor vessel 110, as illustrated by electrical probes 40-1, 40-2, 40-3, 40-4, 40-5, 40-6, 40-7, 40-8, 40-9. Further details of fluidized bed polymerization reactor systems and electrical probes including specific apparatus adapted for such monitoring are described below, and each of the below-described details are specifically considered in various combination with these and other generally preferred approaches described herein.

In another preferred general approach of the general method, a source of an impurity in a moving bulk material is determined. An electrical probe 40 is placed in contact with a moving bulk material 10. The electrical probe is monitored. Based on a monitored response of the electrical probe, the presence of an impurity can be determined. A flow rate of one or more feed streams 111, 113 are altered, and a determination is made as to whether the altering of the flow rate of the feed stream affects the determination of the presence of the impurity. If altering the flow rate of a feed stream affects the determination of the presence of the impurity, the feed stream can be further analyzed to determine whether that feed stream is the source of the impurity.

In yet another preferred general approach of the general method, a source of an impurity in a moving bulk material is determined by contacting an electrical probe with a moving bulk material, monitoring the electrical probe, and determining presence of an impurity based on the monitoring as above. In this general approach, however, a source of at least one feed stream is changed. A determination is made as to whether changing the source of the at least one feed stream affects the determination of the presence of the impurity. If changing the source of a feed stream affects the determination of the presence of the impurity, the original source of the feed stream can be further analyzed to determine whether that original source contains an impurity.

The present invention also includes devices and systems effective for detecting impurities according to the aforementioned methods. In general, such devices are systems or apparatus that comprise one or more electrical probes, including static probes adapted to measure static charge of bulk material in a barrier.

Figure 3:
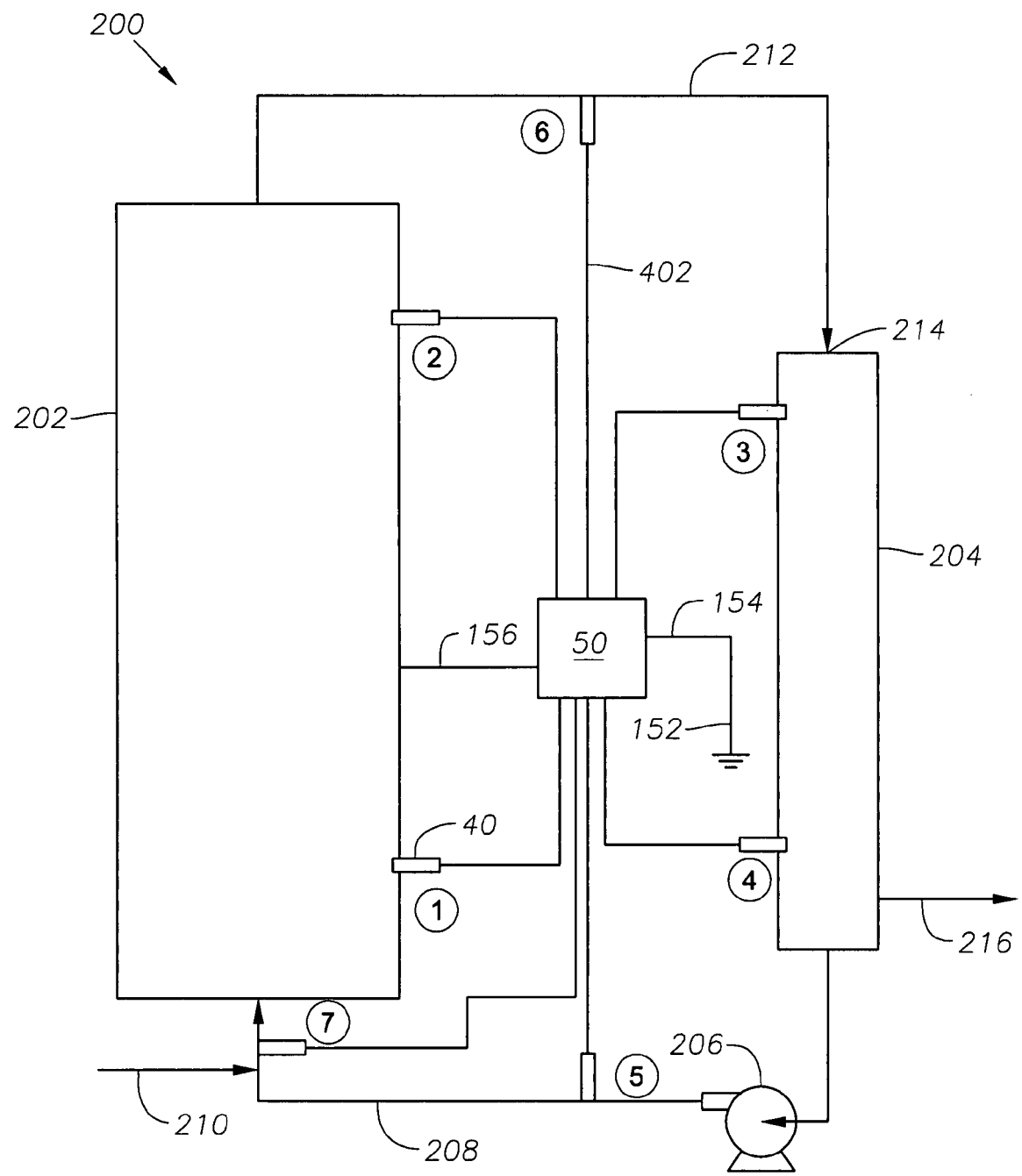
FIG. 3 is a schematic representation of the general methods, systems and/or apparatus of certain embodiments of the invention illustrating implementation in a fluidized bed polymerization reactor.

A preferred general system of the invention can comprise an electrical probe 40 adapted to interface a barrier 15 (e.g., vessel or reactor 110), where the interfaced electrical probe comprises a sensing element, and is in communication with at least one or both of a data retrieval circuit or a signal processing circuit of the processing unit 50 that measures an amperage of a current between the electrical probe and some reference, e.g., ground 152, reactor vessel 110, etc., or equivalently, a voltage differential between the electrical probe and some reference, e.g., ground 152, reactor vessel 110, etc. FIGS. 2 and 3 illustrate connections to both a ground 152 and a reactor vessel 110 via conductors 154, 156, respectively.

In another preferred general embodiment, with reference to FIG. 2, a fluidized bed polymerization reactor system 100 includes a reactor vessel 110 (also referred to interchangeably herewith as a reaction vessel), and may include a recycle line 122. An electrical probe 40 is in contact with a bulk material inside the reactor system. The electrical probe is monitored for determining presence of an impurity.

In another preferred general embodiment, with reference to FIGS. 2 and 3, a fluidized bed polymerization reactor system 100 includes a reactor vessel 110 having a distributor plate 128. An electrical probe 40 is positioned above a hole in the distributor plate. The electrical probe is monitored for determining presence of an impurity.

Monitoring of Single- and Multi-Phase Systems—General Considerations

In each of the aforementioned generally preferred approaches and/or embodiments, the electrical probe(s) can be employed for monitoring a variety of processes, including but not limited to, gas phase, gas/solid phase, liquid/solid phase, gas/liquid phase, and gas/liquid/solid phase reactor systems including polymerization reactor systems; gas phase, gas/solid phase, liquid/solid phase, gas/liquid phase, and gas/liquid/solid phase mass transfer systems; gas phase, gas/solid phase, liquid/solid phase, gas/liquid phase, and gas/liquid/solid phase mixing systems; gas phase, gas/solid phase, liquid/solid phase, gas/liquid phase, and gas/liquid/solid phase heating or cooling systems; gas/solid phase and gas/solid/liquid phase drying systems; etc.

Fluidized Bed Systems (Including Fluidized Bed Polymerization Reactor Systems)

A fluidized bed can generally include a bed of particles in which the static friction between the particles is disrupted. In each of the aforementioned generally preferred approaches and/or embodiments, the fluidized bed system can be an open fluidized bed system or a closed fluidized bed system. An open fluidized bed system can comprise one or more fluids and one or more types of fluidized solid particles and having one or more fluidized bed surfaces that are exposed to an open uncontrolled atmosphere. For example, an open fluidized bed system can be an open container such as an open-top tank or an open well of a batch reactor or of a parallel batch reactor (e.g., microtiter chamber). Alternatively, the fluidized bed system can be a closed fluidized bed system. A closed fluidized bed system can comprise one or more fluids and one or more types of fluidized particles that are generally bounded by a barrier so that the fluids and particles are constrained. For example, a closed fluidized bed system may include a pipeline (e.g., for particle transport); a recirculating fluidized bed system, such as the fluidized bed polymerization reactor system of FIG. 2 (discussed above and below); or a solids drying system; any of which may be associated with various residential, commercial and/or industrial applications.

A closed fluidized bed system can be in fluid communication with an open fluidized bed system. The fluid communication between a closed fluidized bed system and an open fluidized bed system can be isolatable, for example, using one or more valves. Such isolation valves can be configured for unidirectional fluid flow, such as for example, a pressure relief valve or a check valve. In general, the fluidized bed system (whether open or closed) can be defined by manufactured (e.g., man-made) boundaries comprising one or more barriers. The one or more barriers defining manufactured boundaries can generally be made from natural or non-natural materials. Also, in general, the fluidized bed system (whether open or closed) can be a flow system such as a continuous flow system or a semi-continuous flow (e.g., intermittent-flow) system, a batch system, or a semi-batch system (sometimes also referred to as a semi-continuous system). In many instances, fluidized bed systems that are flow systems are closed fluidized bed systems.

The fluidized bed in preferred embodiments is generally formed by flow of a gaseous fluid in a direction opposite gravity. The frictional drag of the gas on the solid particles overcomes the force of gravity and suspends the particles in a fluidized state referred to as a fluidized bed. To maintain a viable fluidized bed, the superficial gas velocity through the bed must exceed the minimum flow required for fluidization. Increasing the flow of the fluidizing gas increases the amount of movement of the particles in the bed, and can result in a beneficial or detrimental tumultuous mixing of the particles. Decreasing the flow results in less drag on the particles, ultimately leading to collapse of the bed. Fluidized beds formed by gases flowing in directions other than vertically include particles flowing horizontally through a pipe, particles flowing downwardly e.g., through a downcomer, etc.

Fluidized beds can also be formed by vibrating or otherwise agitating the particles. The vibration or agitation keeps the particles in a fluidized state.

Fluidized Bed Polymerization Reactor Systems

In each of the aforementioned generally preferred approaches and/or embodiments, a fluidized bed system can include a fluidized bed polymerization reactor system. As briefly noted above, gas phase polymerization reactions may be carried out in fluidized bed polymerization reactors, and can also be formed in stirred or paddle-type reaction systems (e.g., stirred bed systems) which include solids in a gaseous environment. While the following discussion will feature fluidized bed systems, where the present invention has been found to be preferred and especially advantageous, it is to be understood that the general concepts relating to the use of the electrical probes for impurity detection, which are discussed relevant to the preferred fluidized bed systems, are also adaptable to the stirred or paddle-type reaction systems as well. The present invention is not limited to any specific type of gas phase reaction system.

In very general terms, a conventional fluidized bed polymerization process for producing resins and other types of polymers is conducted by passing a gaseous stream containing one or more monomers continuously through a fluidized bed reactor under reactive conditions and in the presence of catalyst at a velocity sufficient to maintain the bed of solid particles in a suspended condition. A continuous cycle is employed where the cycling gas stream, otherwise known as a recycle stream or fluidizing medium, is heated in the reactor by the heat of polymerization. The hot gaseous stream, also containing unreacted gaseous monomer, is continuously withdrawn from the reactor, compressed, cooled and recycled into the reactor. Product is withdrawn from the reactor and make-up monomer is added to the system, e.g., into the recycle stream or reactor vessel, to replace the polymerized monomer. See for example U.S. Pat. Nos. 4,543,399, 4,588,790, 5,028,670, 5,317,036, 5,352,749, 5,405,922, 5,436,304, 5,453,471, 5,462,999, 5,616,661, 5,668,228, and 6,689,847 all of which are fully incorporated herein by reference. A basic, conventional fluidized bed system is illustrated in FIG. 2. The reactor vessel 110 comprises a reaction zone 112 and a velocity reduction zone 114. While a reactor configuration comprising a generally cylindrical region beneath an expanded section is shown in FIG. 2, alternative configurations such as a reactor configuration comprising an entirely or partially tapered reactor may also be utilized. In such configurations, the fluidized bed can be located within a tapered reaction zone but below a region of greater cross-sectional area which serves as the velocity reduction zone of the more conventional reactor configuration shown in FIG. 2.

In general, the height to diameter ratio of the reaction zone can vary in the range of about 2.7:1 to about 5:1. The range may vary to larger or smaller ratios and depends mainly upon the desired production capacity. The cross-sectional area of the velocity reduction zone 114 is typically within the range of from about 2.5 to about 2.9 multiplied by the cross-sectional area of the reaction zone 112.

The reaction zone 112 includes a bed of growing polymer particles, formed polymer particles and a minor amount of catalyst all fluidized by the continuous flow of polymerizable and modifying gaseous components, including inerts, in the form of make-up feed and recycle fluid through the reaction zone. To maintain a viable fluidized bed, the superficial gas velocity through the bed must exceed the minimum flow required for fluidization which is typically from about 0.2 to about 0.5 ft/sec. for polyolefins. Preferably, the superficial gas velocity is at least 0.2 ft/sec above the minimum flow for fluidization or from about 0.4 to about 0.7 ft/sec. Ordinarily, the superficial gas velocity will not exceed 5.0 ft/sec and is usually no more than about 2.5 ft/sec.

On start-up, the reactor is generally charged with a bed of particulate polymer particles before gas flow is initiated. Such particles help to prevent the formation of localized "hot spots" when catalyst feed is initiated. They may be the same as the polymer to be formed or different. When different, they are preferably withdrawn with the desired newly formed polymer particles as the first product. Eventually, a fluidized bed consisting of desired polymer particles supplants the start-up bed.

Fluidization is achieved by a high rate of fluid recycle to and through the bed, typically on the order of about 50 times the rate of feed or make-up fluid. This high rate of recycle provides the requisite superficial gas velocity necessary to maintain the fluidized bed. The fluidized bed has the general appearance of dense mass of individually moving particles as created by the percolation of gas through the bed. The pressure drop through the bed is equal to or slightly greater than the weight of the bed divided by the cross-sectional area.

Referring again to FIG. 2, make-up fluids can be fed at points 118 and 119 via recycle line 122. The composition of the recycle stream is typically measured by a gas analyzer 121 and the composition and amount of the make-up stream is then adjusted accordingly to maintain an essentially steady state composition within the reaction zone. The gas analyzer 121 can be positioned to receive gas from a point between the velocity reduction zone 114 and heat exchanger 124, preferably, between compressor 130 and heat exchanger 124.

To ensure complete fluidization, the recycle stream and, where desired, at least part of the make-up stream can be returned through recycle line 122 to the reactor, for example at inlet 126 below the bed. Preferably, there is a gas distributor plate 128 above the point of return to aid in fluidizing the bed uniformly and to support the solid particles prior to start-up or when the system is shut down. The stream passing upwardly through and out of the bed helps remove the heat of reaction generated by the exothermic polymerization reaction.

The portion of the gaseous stream flowing through the fluidized bed which did not react in the bed becomes the recycle stream which leaves the reaction zone 112 and passes into the velocity reduction zone 114 above the bed where a major portion of the entrained particles drop back onto the bed thereby reducing solid particle carryover.

The recycle stream is then compressed in compressor 130 and passed through heat exchanger 124 where the heat of reaction is removed from the recycle stream before it is returned to the bed. Note that the heat exchanger 124 can also be positioned before the compressor 130. The recycle stream exiting the heat exchange zone is then returned to the reactor at its base 126 and thence to the fluidized bed through gas distributor plate 128. A fluid flow deflector 132 is preferably installed at the inlet to the reactor to prevent contained polymer particles from settling out and agglomerating into a solid mass and to maintain entrained or to re-entrain any particles or liquid which may settle out or become disentrained.

In this embodiment, polymer product is discharged from line 144. Although not shown, it is desirable to separate any fluid from the product and to return the fluid to the reactor vessel 110.

In accordance with an embodiment of the present invention, the polymerization catalyst enters the reactor in solid or liquid form at a point 142 through line 148. If the catalyst requires the use of one or more co-catalysts, as is usually the case, the one or more cocatalysts may be introduced separately into the reaction zone where they will react with the catalyst to form the catalytically active reaction product. However the catalyst and cocatalyst(s) may be mixed prior to their introduction into the reaction zone.

The reactor shown in FIG. 2 is particularly useful for forming polyolefins such as polyethylene, polypropylene, etc. Process conditions, raw materials, catalysts, etc. for forming various polyolefins and other reaction products are found in the references incorporated herein. Illustrative process conditions for polymerization reactions in general are listed below to provide general guidance.

The reaction vessel, for example, has an inner diameter of at least about 2 feet, and sometimes greater than about 10 feet.

The reactor pressure in a gas phase process may vary from about 100 psig (690 kPa) to about 600 psig (4138 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated include series or multistage polymerization processes. Also gas phase processes contemplated by the invention include those described in U.S. Pat. Nos. 5,627,242, 5,665,818 and 5,677,375, and European publications EP-A-0 794 200, EP-B1-0 649 992, EP-A-0 802 202, and EP-B-634 421 all of which are herein fully incorporated by reference.

In an embodiment, the reactor utilized in the present invention is capable of producing greater than 500 lbs of polymer per hour (227 Kg/hr) to about 300,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Another illustrative fluidized bed polymerization reactor system 200 is shown in FIG. 3. As shown, the system 200 is a recirculating system including a fast riser 202, a downcomer 204, and a recirculating pump 206. The monomer(s) and catalyst are added to recycle line 208 via feed 210. In this type of system, the polymerization product is formed primarily in the fast riser, but continues to form throughout the system. Polymer particles formed in the fast riser 202 pass through line 212 to an upper inlet port 214 of the downcomer 204. The polymer particles gather in the downcomer, where they move downwardly in a dense, slow moving bed. The bed formed in the downcomer can be considered a fluidized bed. Particulate polymer product is discharged from line 216. Although not shown, it is desirable to separate any fluid from the product and to return the fluid to the reactor system 200.

Other Types of Bed Systems

Slower moving masses of particles, while considered "fluidized" for purposes of the invention, are also referred to in the art as "moving beds." Moving beds include particles in such things as mass flow bins, downcomers, etc. where solids are slowly moving through a vessel.

Stirred bed system, while considered "fluidized" for purposes of the invention, include beds stirred or otherwise agitated by a member such as a paddle or plunger rotating or moving through the bed (e.g., stirred bed reactor, blender, etc.). Other types of stirred bed systems can be formed by a rotating drum (e.g., with or without internal baffles to enhance mixing), a vessel moving in a see-saw manner, agitation including ultrasonic vibrations applied to the particles or their container, etc.

Fluids

In general, for example, electrical probes can be used in connection with liquids and/or gasses having a wide range of fluid properties, such as a wide range of viscosities, densities and/or dielectric constants (each such property being considered independently or collectively as to two or more thereof). For example, liquid fluids can generally have viscosities ranging from about 0.1 cP to about 100,000 cP, and/or can have densities ranging from about 0.0005 g/cc^3 to about 20 g/cc^3 and/or can have a dielectric constant ranging from about 1 to about 100. In many embodiments of the invention, the bulk material is a gaseous fluid. Gaseous fluids can, for example, generally have viscosities ranging from about 0.001 to about 0.1 cP, and/or can have densities ranging from about 0.0005 to about 0.1 g/cc^3 and/or can have a dielectric constant ranging from about 1 to about 1.1.

The bulk material can include relatively pure gaseous elements (e.g., gaseous $N_2$, gaseous $O_2$). Other components can include relatively pure liquid, solid, or gaseous compounds (e.g., liquid or solid catalyst, gaseous monomer, air). The various systems of the inventions can also include single-phase or multi-phase mixtures of gases, solids and/or liquids, including for example: two-phase mixtures of solids and gases (e.g., fluidized bed systems), mixtures of gasses with a single type of particle, mixtures of gasses with different types of particles (e.g., polymer and catalyst particles); and/or three-phase mixtures of gasses, liquids and solids (e.g., fluidized bed with liquid catalyst being added). Particular examples of preferred fluids are described herein, including in discussion below regarding preferred applications of the methods and devices of the invention.

Impurities

The impurities sought to be detected by the present invention include any type of impurity capable of being detected by the general methods presented herein in any of the various types of systems described herein.

In a polyolefin production reactor system, small amounts of impurities in feedstock, even at sub-ppm levels, can adversely affect reactor operations by deactivating the catalyst. Other effects such as static generation also have been attributed to low levels of impurities. Typical feedstocks which may be contaminated with impurities include the primary monomer (e.g., ethylene), comonomers (e.g., linear alpha-olefins), hydrogen, induced condensing agents (e.g., butane, isobutane, isopentane, hexane, isohexane, and fluorinated compounds), and inerts (e.g., nitrogen, helium, methane, ethane).

Impurities in gaseous feedstocks include but are not limited to $H_2O$, $O_2$, CO, $CO_2$, acids, sulfur compounds and other polar compounds. Heavier feedstocks such as comonomers and induced condensing agents typically have these impurities as well as heavier compounds such as isomeric forms of the feedstock molecule or by-products from production operations. Illustrative "active" impurities which can impact operations by deactivating catalyst and influencing polymerization reactions include, but are not limited to, $H_2O$, $O_2$, CO, $CO_2$, acids, sulfur compounds and other polar compounds.

Although the aforementioned examples are listed as impurities, one skilled in the art will recognize that in certain embodiments for a variety of polymerization processes employing a wide variety of catalyst systems and for a given polymer product, some of the examples provided above may be desirable components of a polymerization process under a controlled environment. Thus, the ability to detect an impurity for these embodiments becomes of greater importance. Additionally, merely listing an example above as an impurity should not be read to necessarily exclude the example from its utilization in an inventive polymerization process.

While not wishing to be bound to any particular theory, the inventors believe that some "active" impurities derive their reactivity, in part, from unshared electrons available for donation to reactive species such as catalyst active sites. These electron rich species are often referred to as "polar" compounds. This electronic characteristic often imparts an electrical dipole moment in the molecule. The inventors believe that the electrical dipole moment in the molecule are detected even at parts-per-million and parts-per-billion levels with sensors designed to be sensitive to bulk material properties such as dielectric constant, as disclosed herein. The inventors wish to emphasize that the foregoing theory may not apply to every impurity detectable by the embodiments disclosed herein.

In preferred embodiments of the present invention, the bulk material consists essentially of nonpolar materials, while the impurities that are detected are polar. For example, in a polyolefin reactor system such as that shown in FIG. 2, the feedstocks and reaction products are nonpolar. In other embodiments, the bulk material may contain some desired polar materials. In such embodiments, at steady state, the sudden introduction or withdrawal of an impurity is detected as a change in electrical characteristic of the electrical probe, as described above and below.

Inert impurities may also be controlled to avoid accumulation in the reactor but do not directly impact operations by catalyst deactivation reactions or significant modification of the polymerization reactions.

Operating Conditions

The operating conditions of the reactor and other systems are not narrowly critical to the invention. While general operating conditions have been provided above for fluidized bed polymerization reactor systems, fluidized and nonfluidized bed systems can, in addition to those listed above, have widely varying process conditions, such as temperature, pressure, fluid flowrate, etc.

Electrical Probes

In general, as noted above, the particular electrical probe of the methods and systems and apparatus of the present invention is not limited. Generally, the electrical probes useful in connection with this invention are adapted to be in contact with a bulk material. By monitoring the electrical probe, the presence of impurities in the bulk material can be detected. By "monitoring" what is meant is to generate data associated with an electrical response of the electrical probe. The data association with the electrical response in this context means data (typically obtained or collected as a data stream over some time period such as a sensing period), including both raw data (directly sensed data, e.g., level of current or voltage) or processed data, can be directly informative of or related to (e.g., through correlation and/or calibration) an absolute value of a property and/or a relative value of a property (e.g., a change in a property value over time), and can be used to determine the presence of an impurity. In many applications, the raw data can be associated with a property of interest using one or more correlations and/or using one or more calibrations. Typically such correlations and/or calibrations can be effected electronically using signal processing circuitry, either with user interaction or without user interaction (e.g., automatically).

Particular electrical probes can be selected based on a needed or desired property (or properties) of interest, and on required specifications as to sensitivity, universality, fluid-compatibility, system-compatibility, as well as on business considerations such as availability, expense, etc.

The electrical probe can include, for example, an electrically conductive member or surface designed to contact a bulk material. Various types of electrical probes can be employed, including for example the electrical probes shown in FIGS. 4 and 5, or combinations thereof.

Figure 4:
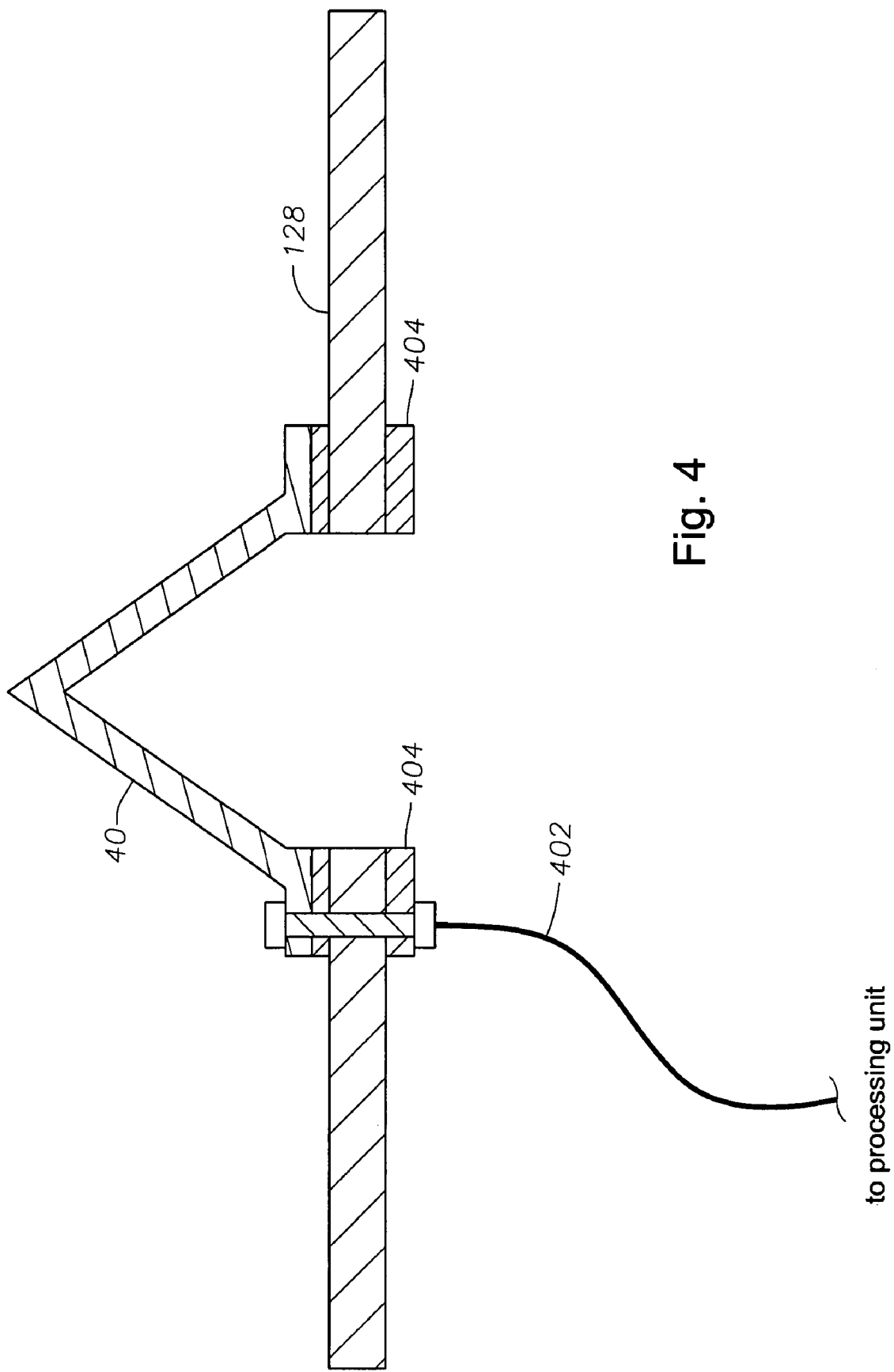
FIG. 4 is a schematic representation of an apparatus of an embodiment of the invention.

An electrical probe 40 in one approach is shown in FIG. 4 and described in U.S. Pat. No. 6,831,140 to Muhle et al., which is herein fully incorporated by reference. FIG. 4 shows a schematic drawing of a side-view of an electrical probe 40 of the present invention that may be installed on the distributor plate 128 of a reactor vessel. A top view would show a hole in the plate of approximate size ⅝ inch, although any hole size would be appropriate. The electrical probe covers the hole and extends on each side about 1 inch, although any length would be appropriate. The electrical probe may be a metallic conductor, such as carbon steel or stainless steel; a ceramic conductor; etc. In FIG. 4, the electric probe is shown in a triangular shape or as an "angle iron". Other shapes also could be utilized such as a circular one ("pipe cap") or T-cap also termed a tuyere.

The plate cap version of the electrical probe 40 shown in FIG. 4 is in a high impact area. For example, at a nominal reactor superficial velocity of 2.0 ft/sec the electrical probe experiences a hole velocity of 118 ft/sec. It therefore serves as a primary source of frictional triboelectrification. The electrical probe is electrically insulated from the plate because the electrical probe is grounded (e.g., charge generation lead to short circuit to ground). Thus, insulators 404 are placed between the electrical probes and the distributor plate. Any insulator is contemplated, preferred insulators being thermally and chemically stable. A non-limiting example of a suitable insulator is polytetrafluoroethylene (Teflon®). The electrical lead 402 connected to the electrical probe 40 is shown at the bottom using a bolt with an insulated sleeve to contact the top plate. The sleeve isolates the bolt from the plate and provides electrical contact with the plate cap. Alternatively, the electrical connection may be made at the upper end of the plate cap, if desired. The electrical lead 402 is also connected to the processing unit 50.

Figure 5:
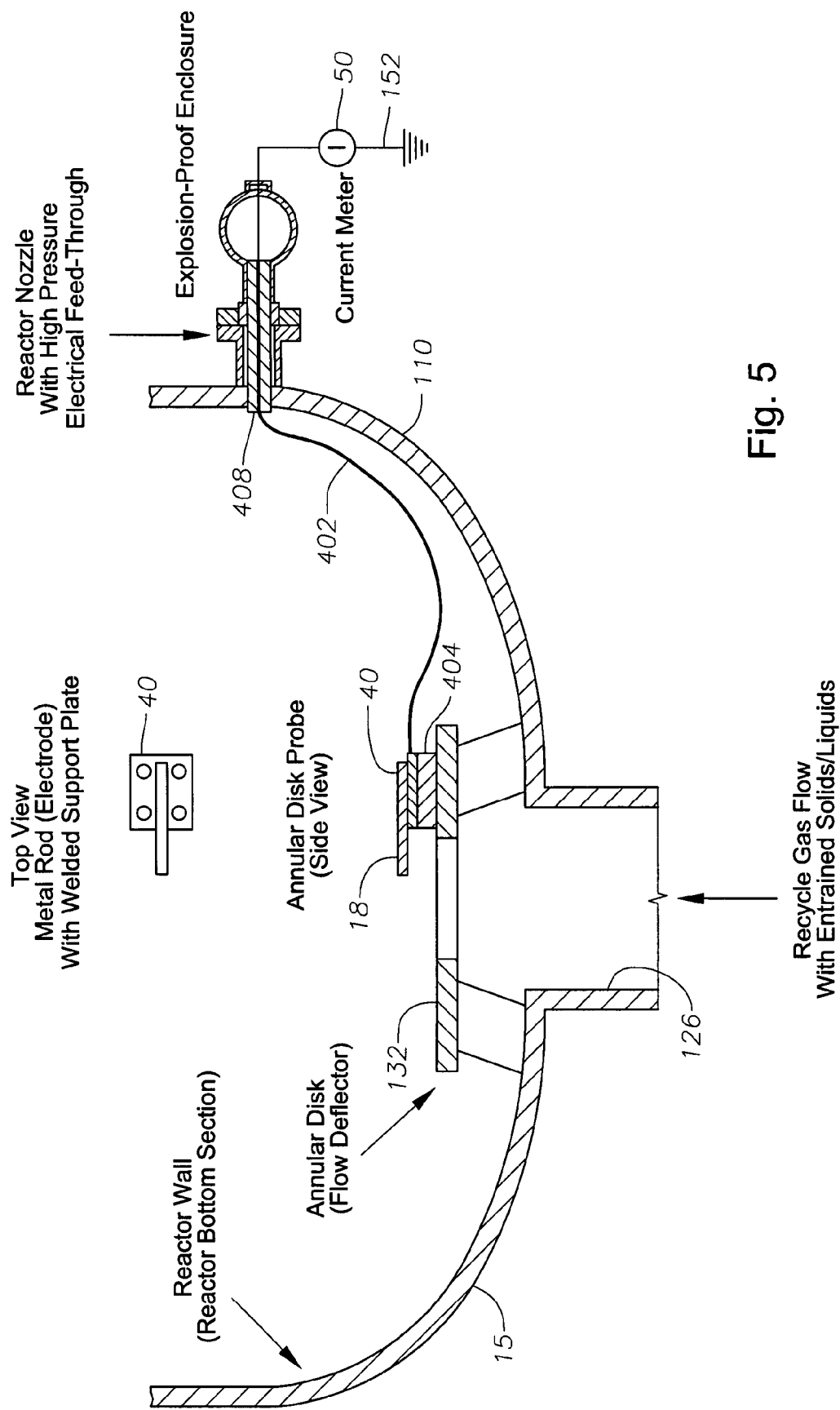
FIG. 5 is a schematic representation of an apparatus of an embodiment of the invention.

In another approach, with reference to FIGS. 1 and 5, an electrical probe 40 includes an electrically conductive member 18 coupled to but preferably insulated from the barrier 15. With reference to FIG. 5, the electrical probe in one preferred embodiment includes an electrically conductive rod coupled to a support plate, e.g., by welding. The support plate may be electrically isolated from an electrically conductive barrier 15, in this case the reactor vessel 110, by an insulator 404. The electrical lead 402 is connected to the processing unit 50.

In a further approach, the electrical probes may include a rod with a ball on the end of the rod.

Some or all of the electrical probes in the various embodiments may be coupled to ground. Switches, resistors, and other components may be present between the electrical probes and ground. The ground may be a true ground, or may be biased to some potential. In other approaches, the ground may be the barrier 15 itself, such as the reactor vessel of a polymerization reactor system. In one approach, the amperage of the current passing from the electrical probe and ground can be monitored for indication of presence of an impurity. In another approach, the voltage differential between the electrical probe and ground can be monitored for indication of presence of an impurity. In other embodiments, some or all of the electrical probes are isolated from a ground.

While the electrical probe 40 is described above and below in terms of being coupled to an external processing unit 50, the circuitry may also be implemented with the electrical probe in a single standalone unit. As one preferred example, the electrical probe 40 may comprise an electrical probe, a signal processing circuit (e.g., comprising amplifier circuitry), and/or a data retrieval circuit (e.g. comprising data memory circuitry, perhaps adapted for recording raw data received from the electrical probe).

Probe Positioning

With further reference to FIGS. 1, 2, 3, 4 and 5 in an embodiment, the electrical probes 40 can be placed in many different positions along or in the system containing the bulk material.

In certain embodiments, it is advantageous to locate an electrical probe for impurity detection inside the process instead of feed points to the process. In this way, it is possible to identify and troubleshoot causes of impurities which occur inside the process. Process-related impurities can include impurities introduced to the process during maintenance (when a portion of the process may be opened to atmosphere for work) as well as impurities present during startup such as traces of ambient air and reactor kill gases. Further, locating the probes inside the system allows them to detect impurities in any feedstock to the system. This eliminates the need for multiple, dedicated detectors on each feed stream. In the fluidized bed polymerization reactor system 100 of FIG. 2, for example, most fresh feedstock is fed to the process by injection into the recycle line 122 linking top and bottom of the reactor vessel 110. The injection point is usually located at a point on the recycle line as it nears the inlet 126 at the bottom of the reactor vessel. An electrical probe located near the inlet is in direct contact with the flowing stream between the feedstock injection point and the fluidized bed. At this location the probe is in continuous contact with both the reactor "cycle gas" as well as the fresh feed entering the recycle line and reactor.

In the fluidized bed polymerization reactor system 100 of FIG. 2, for example, some electrical probes, e.g., 40-1, 40-2, 40-3, 40-4, 40-5, 40-6, 40-7 have sensing surfaces positioned in the reactor vessel 110. Other electrical probes e.g., 40-8, 40-9, 40-10, can be positioned at virtually any position along the recirculation system. Electrical probes 40-3, 40-4, 40-5, 40-6 are ported sensors that pass through the reactor vessel 110 such that the sensing surface of each electrical probe 40 is exposed to the fluidized particles in the reaction zone 112. Electrical probe 40-7 is a ported sensor having a sensing surface exposed to the bulk material in the velocity reduction zone 114.

In particularly preferred embodiments, an electrical probe 40 is located between the feedstock feed lines and a primary reaction zone. This positioning allows detection of an impurity in the feedstock before the impurity is consumed in a reaction with the catalyst or other component in the bulk material.

Electrical probe 40-1 is mounted above a hole in the distributor plate 128, as also shown in FIG. 4. The electrical probe is in direct contact with the hydrocarbon stream rising through the hole and is electrically insulated from the distributor plate. The electrical probe may also function as a static probe, as described in U.S. Pat. No. 6,831,140 to Muhle et al., which is herein incorporated by reference.

The electrical probe in one embodiment of the present invention is capable of performing the dual roles of impurity detection and static level measurement. For example, monitoring of static changes in a fluidized bed gas phase reaction is a useful method for detecting changes in the reactor which indicate the onset of discontinuities such as sheeting. The sooner these changes can be detected, sooner corrective action can be taken, thereby reducing the chances of a discontinuity in the reactor. Thus, such an embodiment allows detection of changes in the static charges in the reactor early on. This early detection allows for better control of the reactor.

Generally, the gas distributor plate serves to ensure proper gas distribution and to support the resin bed when gas flow is stopped. For example, during operation of the reactor and after a catalyst(s) and polymerizable materials have been introduced into the reactor, cycle gas enters the bottom of the reactor and passes upward through a gas distributor plate into a fluidized bed located in the straight-sided section of the vessel. Gas leaving the fluidized bed entrains resin particles, and most of these particles are disengaged as the gas passes through the expanded section where its velocity is reduced. Measurements taken at the distributor plate using the static probe of the present invention have indicated that the velocity is 10-100 times that in the bed. Because metal-to-polymer contact occurs on the plate, charge transfer from dissimilar materials is more likely to occur. Taken together, the net result is a massive charge generation at the plate relative to the bed.

The electrical probe of FIG. 4, when operating as a static probe, provides a measure of overall reactor vessel wall condition in two respects. First, reactors operating with a good wall condition do not have a high plate static value in either a positive or negative charge sense. Secondly, the static level differences between the reactor and plate probe may be small and/or of the same sign, but remain within the limit of detection of the inventive probe. A static level that is indicative of a poor reactor wall condition or of an abnormal operation include at least one of a large fluctuation about zero for both the plate and reactor static probe; sign reversal between the plate and reactor static probes; and readings that alter from about zero, i.e. from the zero baseline.

The distributor plate design may vary to effect the desired fluidization and/or thermodynamics of the polymerization reaction. Specifically, a distributor plate that comprises a plurality of pores may be used to decrease pressure, particularly at higher velocities. It is also contemplated that conventional static probes (and/or detector designs similar to those as herein defined) be located throughout the recycle system (e.g. at the compressor, heat exchanger/cooler and/or in recycle transfer lines) in addition to at the distributor plate.

With continued reference to FIG. 2, electrical probe 40-2 is mounted to the flow deflector, as also shown in FIG. 5. This electrical probe is located at the inlet of the reactor and is in direct contact with the flowing hydrocarbon stream as it enters the expansion zone just below the distributor plate. In a preferred embodiment, the electrical probe extends several inches into the flowing stream. The electrical probe shown in FIGS. 2 and 5 may also function as a static probe. The electrically conductive rod serves as an electrode. Entrained solid and liquid particles in the recycle flow impact the electrode and transfer electrical charge. The rate of charge flow can be measured as a current signal or equivalently a voltage differential by the processing unit 50.

Electrical probes 40-3, 40-4, 40-5, 40-6, 40-7 40-8, 40-9, 40-10 may take the form of any of the electrical probes described above and below, and may be used to detect impurities and/or static levels.

With continued referenced to FIG. 2, electrical probes 40-8, 40-9, 40-10 are positioned in the recycle system. While the electrical probes are shown as on the recycle line 122, electrical probes can also be positioned in the various components such as in the heat exchanger 124.

With reference to FIG. 3, electrical probes 40-1, 40-2, 40-3, 40-4, 40-5, 40-6, 40-7 are positioned in the fast riser 202, downcomer 204 and recirculation lines 208, 212.

In various embodiments, an electrical probe of the present invention located at one position may be used in combination with at least one other electrical probe to provide, for example, a comparative measure of impurity concentration and/or source. More particularly, the extent of signal change of each probe is measured. Calculating the difference in the net signal change for each probe is then used to determine the difference between two probes. This in turn provides a net measure of the impurity levels at the various locations in the system. For example, referring to FIG. 2, the current of electrical probe 40-2 can be compared to the current of electrical probe 40-8. If an impurity is detected at electrical probe 40-2, but not at electrical probe 40-8, it is likely that the impurity is reacting with the catalyst. In another example, the current of electrical probe 40-2 can be compared to the current of electrical probe 40-10. If an impurity is detected at electrical probe 40-2, but not at electrical probe 40-10, it is likely that the impurity is being introduced by feedstock feed stream 111 and not feedstock feed stream 114.

Processing Unit

With reference to FIGS. 1, 2, 3 and 5, the processing unit 50 is coupled to the leads 402 from the electrical probes. The processing unit 50 may be a simple monitoring device. Illustrative processing units 50 include an electrometer or low current meter (picoammeter), a digital volt meter, an ohmmeter, an oscilloscope, or the like. More complex processing units are also contemplated, such as computerized systems. The processing unit may be coupled to other system components 160 such as process controllers.

In preferred embodiments, one or more circuit modules of the signal processing circuit and/or the data retrieval circuit can be implemented and realized as an application specific integrated circuit (ASIC). Portions of the processing can also be performed in software in conjunction with appropriate circuitry and/or a host computing system.

As mentioned above, while the electrical probe 40 is described above and below in terms of being coupled to an external processing unit 50, the circuitry may also be implemented with the electrical probe in a single standalone unit. As an example, the electrical probe 40 may comprise an electrical probe, a signal processing circuit (e.g., comprising amplifier circuitry), and/or a data retrieval circuit (e.g. comprising data memory circuitry, perhaps adapted for recording raw data received from the electrical probe).

In one approach, during steady-state operations, the processing unit measures about a constant voltage or current between a ground and the electrical probe. A change in the level of impurities is detected as a change in the amperage.

In another approach, during steady-state operations, the processing unit measures about a constant voltage differential between a ground and the electrical probe. A change in the level of impurities is detected as a change in the voltage of the electrical probe.

Barrier Interface

As described above in connection with the methods, systems, and apparatus (e.g., in connection with FIGS. 1, 2 and 3), a ported electrical probe or ported electrical probe subassembly can be interfaced with the fluidized or nonfluidized system across a barrier 15 that defines at least a portion of the fluidized or nonfluidized system. Preferably, the ported electrical probe, the electrical probe or electrical probe subassembly is interfaced across the barrier without substantially compromising the integrity of the barrier.

With reference to FIGS. 4 and 5, in some embodiments, the electrical probe 40 is connected to an electrical lead 402 which is routed to a reactor vessel exit point which is designed to insulate the electrical lead from the reactor body. For example, the electrical lead may be from the high pressure reactor environment through a mechanical seal 408 which is or includes an insulator. In some embodiments, a pressure sealing gland, such as those commercially available from Conax Buffalo Technologies, Buffalo, N.Y., may be used as the insulator/seal 408 at the exit point.

The electrical lead 402 may be housed in an insulative covering. With reference to FIG. 5, in embodiments where the electrical lead is positioned inside the barrier 15, a protective covering may be provided. The protective covering may replace or supplement an insulative covering (if any). An illustrative electrical lead includes a mineral insulation cable.

General Monitoring Applications

The methods and systems and apparatus of the invention can be used to detect impurities in various systems. The invention can be advantageously used, for example, to detect impurities in bulk materials. The invention in some embodiments can also advantageously be used to characterize a level of static charge in a system.

As described above in connection with the generally preferred approaches, systems, and apparatuses (e.g., in connection with FIGS. 1, 2, 3, 4 and 5), the electrical probe is interfaced with one or more bulk materials. The electrical probe is operational for detecting an impurity in the bulk material. The impurity detection can be performed in real time, in near real time, or in time-delayed modes of operation.

Monitoring of Systems-Specific Considerations

Impurity Detection

In the methods and systems and apparatuses of the invention, the particular impurity being detected is not narrowly critical. In general, the impurity of interest will depend on the composition of the bulk material and the significance of the monitoring with respect to a system in a particular commercial application. The monitoring for a particular system may also depend to some extent on the location of the electrical probe. For example, as mentioned above, an impurity may react with a component of the bulk material as it progresses along a barrier, such that the concentration of the impurity becomes less and less as the bulk material flows along the barrier. Accordingly, in some embodiments, the preferred position of the electrical probe is near to, and downstream from, a potential source of the impurity.

In any of the approaches described herein (above and below), the response of the electrical probe may be caused by the contact of the bulk material against the electrical probe alone (passive mode), or by a combination of the contact of the bulk material and an external stimulus (active mode). Further, where multiple electrical probes are present at different positions along the barrier and/or in the bed, the electrical probe responses may be used to determine relative measurements. For example, the responses of electrical probes 40-1 and 40-5 of FIG. 2 can indicate a relative concentration of an impurity at the bottom of the reaction zone to the concentration of the impurity at the top of the reaction zone without the need to quantify the data.

In a passive mode, no external electrical signal is applied to the electrical probe. The electrical probe becomes charged by contact with the bulk material thereagainst. For example, electrical probes 40-2, 40-8, 40-9 and 40-10 in FIG. 2 become charged primarily by contacting entrained solids in the recycle gas. Electrical probes 40-1, 40-3, 40-4, 40-5, 40-6 become charged primarily by contacting solids in the fluidized bed. In one approach, during steady-state operations, a current or voltage will be generated between the electrical probe and ground at a relatively constant level. Introduction, removal, or change in concentration of an impurity from the bulk material causes the current or voltage to change. This change in current or voltage reflects presence, absence, or a change in the level of the impurity. In another approach, during steady-state operations, a voltage on the electrical probe will remain at about a constant level. Introduction, removal, or change in concentration of an impurity from the bulk material causes the voltage on the electrical probe to change. This change in voltage reflects presence, absence, or a change in the level of the impurity In an active mode, an external electrical signal is applied to the electrical probe. In one approach, during steady-state operations, a current or voltage is present between the electrical probe and ground at a relatively constant level. Introduction, removal, or change in concentration of an impurity from the bulk material causes the current or voltage to change. This change in current or voltage reflects presence, absence, or a change in the level of the impurity. In another approach, during steady-state operations, a voltage on the electrical probe will remain at about a constant level. Introduction, removal, or change in concentration of an impurity from the bulk material causes the voltage on the electrical probe to change. This change in voltage reflects presence, absence, or a change in the level of the impurity.

Determining a Source of an Impurity

In one embodiment, a source of an impurity in a moving bulk material may be determined by contacting an electrical probe with a bulk material, monitoring the electrical probe, determining whether an impurity is present based on the monitoring, and altering a flow rate of at least one feed stream into the barrier. A determination is made as to whether altering the flow rate of the at least one feed stream affects determination of whether an impurity is present. Note that the step of determining whether an impurity is present may result in the conclusion that an impurity is not present, just as it might result in the conclusion that an impurity is likely present. In one preferred embodiment, the flow rate of a first feed stream may be altered, i.e., increased, reduced or stopped, to determine the effect on the detection of the impurity. If an effect is seen, it is likely that the source of the impurity is the first feed stream. If altering the flow rate of the first feed stream has no effect, the flow rates of other feed streams can be sequentially altered. In other embodiments, the flow rates of multiple feed streams can be altered simultaneously. In yet other embodiments, this may even include altering the flow rate of all feed streams concurrently. If other feed streams are to be checked for presence of impurities even after one feed stream is suspected of containing an impurity, the flow rate of each feed stream may be sequentially altered. The flow rate of any suspect feed stream can be stopped, altered or reinstated.

In another approach, a source of an impurity in a moving bulk material may be determined by contacting an electrical probe with a bulk material, monitoring the electrical probe, determining whether an impurity is present based on the monitoring, and altering a source of at least one feed stream into the barrier. A determination is made as to whether altering the source of the at least one feed stream affects determination of whether an impurity is present. Note that the step of determining whether an impurity is present may result in the conclusion that an impurity is not present, just as it might result in the conclusion that an impurity is likely present. In one preferred embodiment, the source of a first feed stream may be altered, e.g., changed to another source, partially stopped as to one or more subsources, etc., to determine the effect on the detection of the impurity. If an effect is seen, it is likely that the source of the impurity is the first feed stream. If altering the source of the first feed stream has no effect, the sources of other feed streams can be sequentially altered. In other embodiments, the sources of multiple feed streams can be altered simultaneously. In yet other embodiments, this may even include altering the sources of all feed streams concurrently. If other feed streams are to be checked for presence of impurities even after one feed stream is suspected of containing an impurity, the source of each feed stream may be sequentially altered. The source of any suspect feed stream can be stopped, altered or reinstated.

In another approach, the flow rate of a suspect feed stream may be repeatedly modulated (e.g. turned on and off, increased then decreased then increased, etc.). If an impurity is present in the feed stream, the flow rate modulation produces a corresponding modulation of the amperage/voltage of the electrical probe.

In a further approach, the source of a suspect feed stream may be repeatedly changed. If an impurity is present in the feed stream, the source modulation produces a corresponding modulation of the amperage/voltage of the electrical probe.

It should be kept in mind that various steps performed in the methodology presented herein may be performed in any combination in each of the various combinations and permutations of the present invention.

EXAMPLES

The following description of experimental data is provided by way of example only and is not meant to be limiting.

In each of the following examples, electrical probe measurements were made in an operable polyethylene reactor system similar to that shown in FIG. 2. Electrical probe A was positioned at the inlet of the reactor vessel in direct contact with the flowing recycle stream as it enters the expansion zone just below the distributor plate. The probe extended 6 inches into the flowing stream and was insulated from its mounting bracket by polytetrafluoroethylene spacers. The electrical probe was connected to an electrical lead which was routed to a reactor exit point which was designed to insulate the electrical lead from the steel reactor body. Electrical probe A was operated in passive mode.

Electrical probe B was mounted above a hole in the distributor plate. It was in direct contact with the stream rising through the hole and was electrically insulated from the distributor plate by polytetrafluoroethylene spacers. It was connected to an electrical lead which was routed to a reactor exit point which was designed to insulate the electrical lead from the steel reactor body. Electrical probe B was operated in passive mode.

With reference to FIG. 6 during routine operations, $H_2O$ contamination in an $N_2$ supply was observed in a process analyzer coupled to the feed stream. The concentration of $H_2O$ in the $N_2$ supply exceeded 10 pap. The contaminated $N_2$ feedstock was fed into the recycle stream at a feed rate of $N_2$ to total recycle flow rate that mimicked routine production. In routine production, less than about 2,000 lbs/hr of $N_2$ is added to a recycle stream of greater than about 1,000,000 lbs/hr.

As shown in FIG. 6, prior to introducing the impurity into the N2 feed stream, both electrical probes had a relatively stable current flow. Shortly after the introduction of the impurity into the N2 feed stream, the current from the electrical probes "spiked," indicating the presence of the impurity.

Figure 7:
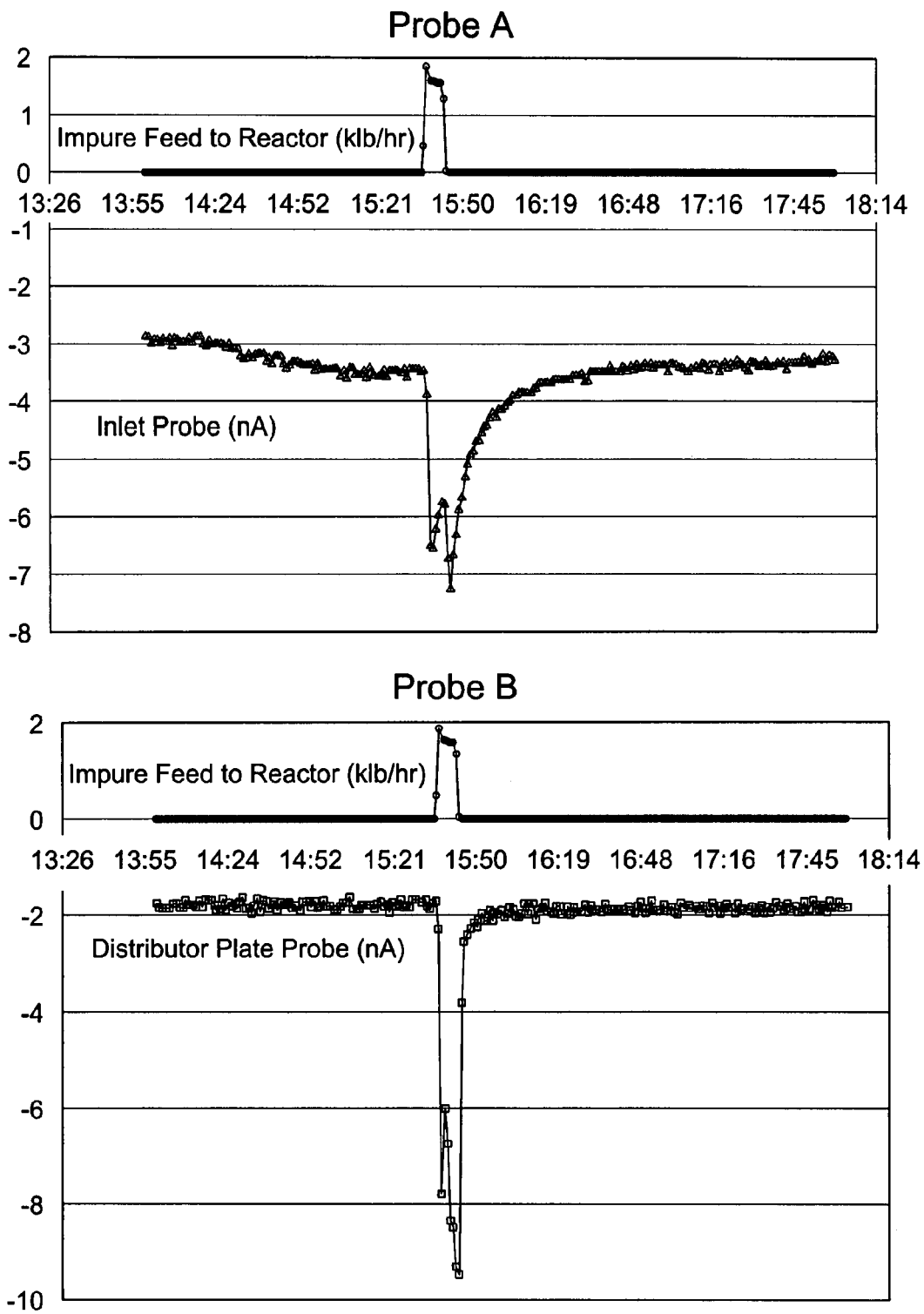
FIG. 7 is a chart reflecting the effect of introduction of an impurity on electrical probes.

With reference to FIG. 7, during routine operations, unknown impurities were suspected in a plant recycle stream consisting primarily of a mixture of high purity nitrogen and high purity ethylene. To test for the presence of impurities, the stream (initially off-line) was fed to the reactor at 1800 lb/hr for six minutes. The presence of impurities in the recycle stream was confirmed by large spikes in both electrical probe A and electrical probe B. After the impurity was removed from the feed stream, the electrical probes tended to return to a steady state current.

Figure 8:
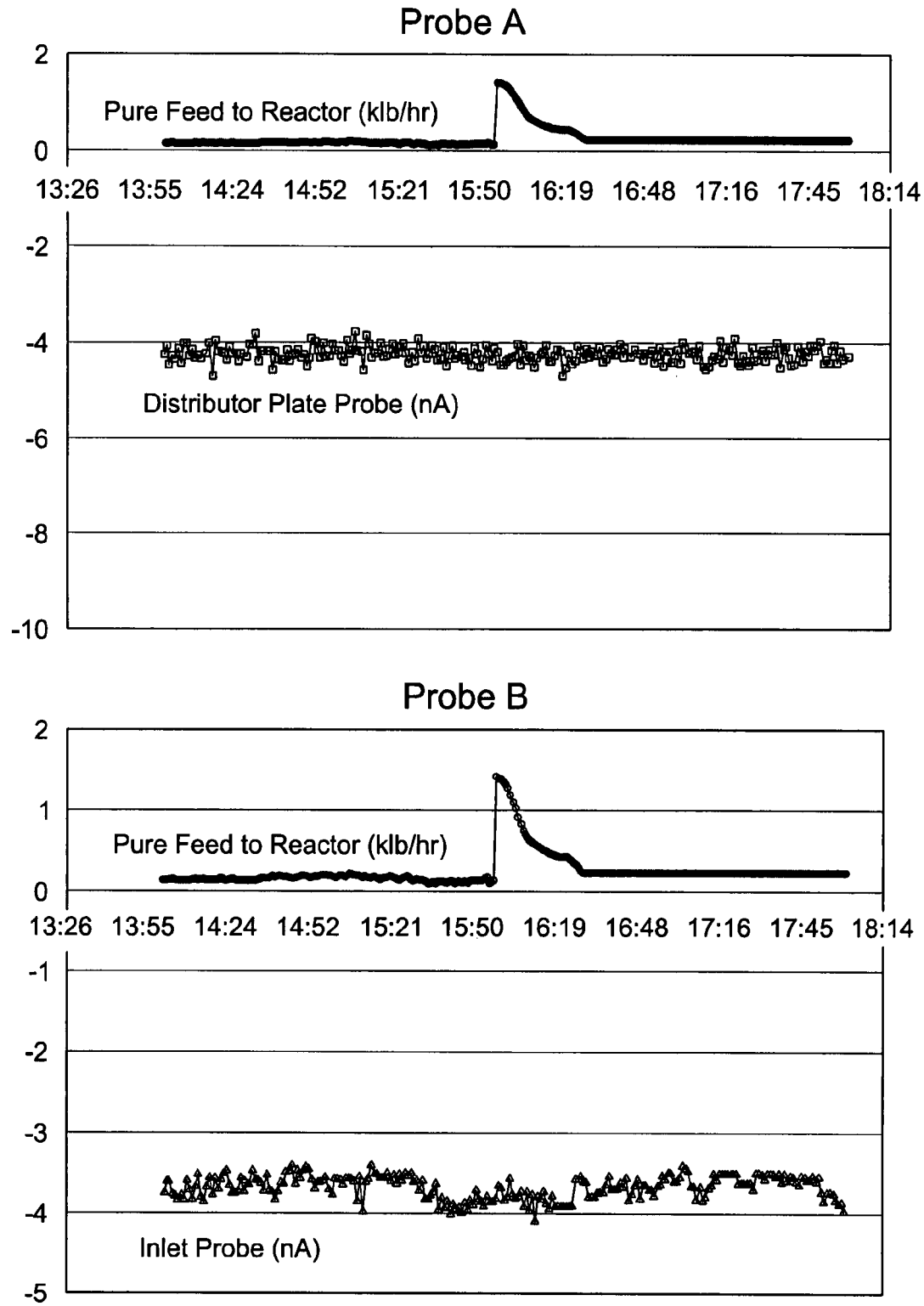
FIG. 8 is a chart reflecting the effect of a change in flow rate of a substantially pure feedstock on electrical probes.

In a comparative experiment, it was found that the electrical probes do not respond to simple flow rate changes, but rather the presence of impurities. With reference to the comparative example shown in FIG. 8, high purity isopentane (initially off-line) was fed to the reactor at 1500 lb/hr initially, then slowly tapered off. No response was observed on either electrical probe A or electrical probe B. Impurities (if any) were present at levels too low to detect. This case shows that the probe does not respond to simple flow rate changes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for detecting at least one impurity in a polymerization reactor system, comprising: contacting at least one electrical probe with a bulk material that includes gaseous and solid phase materials in a reactor vessel in the polymerization reactor system, wherein the reactor vessel has an inner diameter of at least two feet at internal points thereof positioned farthest apart and the pressure in the reactor vessel is in the range of from about 100 psig to about 600 psig; monitoring the electrical probe; and determining the presence of an impurity based on the monitoring.

2. The method as recited in claim 1, wherein the electrical probe is also useable for determining a level of static electricity of solids in the bulk material.

3. The method as recited in claim 2, further comprising using the electrical probe for determining a level of static electricity of solids in the bulk material.

4. The method as recited in claim 1, wherein the bulk material consists essentially of nonpolar materials.

5. The method as recited in claim 4, wherein the impurity is a polar material.

6. The method as recited in claim 1, wherein the impurity is a gaseous material.

7. The method as recited in claim 1, further comprising altering a flow rate of at least one feed stream into the polymerization reactor system, and determining whether the altering of the flow rate of the at least one feed stream affects the determination of the presence of the impurity.

8. The method as recited in claim 1, wherein the electrical probe is positioned above a distributor plate of the polymerization reactor system.

9. The method as recited in claim 1, wherein the electrical probe is positioned between a feedstock inlet and a distributor plate of the polymerization reactor system.

10. The method as recited in claim 9, wherein the feedstock consists essentially of a nonpolar material.

11. The method as recited in claim 1, wherein a second electrical probe is positioned in a recycle line of the polymerization reactor system.

12. The method as recited in claim 1, wherein monitoring the electrical probe includes monitoring a voltage or current flow between the electrical probe and a ground.

13. The method as recited in claim 12, wherein no external electrical signal is applied to the electrical probe, the voltage or current flow being generated by the electrical probe contacting the bulk material.

14. The method as recited in claim 12, wherein the ground is the reactor vessel of the polymerization reactor system.

15. The method as recited in claim 1, wherein monitoring the electrical probe includes detecting a voltage differential between the probe and a ground.

16. The method as recited in claim 15, wherein the ground is the reactor vessel of the polymerization reactor system.

17. The method as recited in claim 1, further comprising monitoring a second electrical probe, determining presence of an impurity based on the monitoring of the second electrical probe, and comparing results of the determining the presence of the impurity based on the monitoring of the electrical probe and the second electrical probe.

18. The method as recited in claim 1, wherein determining the presence of the impurity comprises detecting an electrical property of the impurity.

19. The method as recited in claim 1, wherein determining the presence of the impurity comprises detecting an electrical dipole moment of the impurity.

20. The method as recited in claim 1, wherein determining the presence of the impurity comprises detecting a dielectric constant of the impurity.

21. A method for detecting at least one gaseous impurity in a moving bulk material that includes gaseous and solid phase materials in a gas-phase polymerization reactor wherein the pressure in the reactor is in the range of from about 100 psig to about 600 psig, comprising: contacting at least one electrical probe with a moving bulk material consisting essentially of nonpolar materials; monitoring the electrical probe; and determining the presence of at least one polar impurity based on the monitoring.

22. The method as recited in claim 21, wherein the electrical probe is also useable for determining a level of static electricity of solids in the bulk material.

23. The method as recited in claim 22, further comprising using the electrical probe for determining a level of static electricity of solids in the bulk material.

24. The method as recited in claim 21, wherein monitoring the electrical probe includes monitoring a voltage or current flow between the electrical probe and a ground.

25. The method as recited in claim 24, wherein no external electrical signal is applied to the electrical probe, the voltage or current flow being generated by the electrical probe contacting the bulk material.

26. The method as recited in claim 21, wherein monitoring the electrical probe includes detecting a voltage differential between the probe and a ground.

27. A method for determining a source of at least one impurity in a moving bulk material that includes gaseous and solid phase materials in a gas phase polymerization reactor, wherein the pressure in the reactor is in the range of from about 100 psig to about 600 psig, comprising: contacting at least one electrical probe with a moving bulk material; monitoring the electrical probe; determining whether at least one impurity is present based on the monitoring; altering a flow rate of at least one feed stream; and determining whether the altering of the flow rate of the at least one feed stream affects the determination of whether an impurity is present.

28. The method as recited in claim 27, wherein the altering the flow rate of the at least one feed stream includes reducing the flow rate.

29. The method as recited in claim 27, wherein the altering the flow rate of the at least one feed stream includes stopping the flow rate.

30. The method as recited in claim 27, wherein flow rates of multiple feed streams are altered sequentially.

31. The method as recited in claim 27, wherein flow rates of all feed streams are altered sequentially.

32. The method as recited in claim 27, wherein flow rates of multiple feed streams are altered concurrently.

33. A method for determining a source of at least one impurity in a moving bulk material that includes gaseous and solid phase materials in a gas phase polymerization reactor, wherein the pressure in the reactor is in the range of from about 100 psig to about 600 psig, comprising: contacting at least one electrical probe with a moving bulk material; monitoring the electrical probe; determining whether at least one impurity is present based on the monitoring; altering a source of at least one feed stream; and determining whether the altering the source of the at least one feed stream affects the determination of whether an impurity is present.

34. The method as recited in claim 33, wherein sources of multiple feed streams are altered sequentially.

35. The method as recited in claim 33, wherein sources of all feed streams are altered sequentially.

36. The method as recited in claim 33, wherein sources of multiple feed streams are altered concurrently.

37. A gas-phase polymerization reactor system, comprising:
- at least one reactor vessel having an inner diameter of at least two feet between internal points thereof positioned farthest apart and is capable of being operated at pressures in the range of from about 100 psig to about 600 psig; and
- at least one electrical probe in contact with a bulk material that includes gaseous and solid phase materials inside the reactor system; and
- a processing unit that is in electrical communication with the at least one electrical probe in contact with the bulk material, which monitors the at least one electrical probe to determine the presence of at least one impurity in the bulk material.

38. The reactor system as recited in claim 37, wherein the electrical probe is also useable for determining a level of static electricity of solids in the bulk material.

39. The reactor system as recited in claim 37, wherein the bulk material consists essentially of nonpolar materials.

40. The reactor system as recited in claim 39, wherein the impurity is a polar material.

41. The reactor system as recited in claim 37, wherein the impurity is a gaseous material.

42. The reactor system as recited in claim 37, further comprising at least one feed stream for injecting feedstock into the reactor system, wherein a flow rate of the at least one feed stream into the reactor system is altered for determining whether the altering of the flow rate of the at least one feed stream affects the determination of the presence of the impurity.

43. The reactor system as recited in claim 37, wherein the electrical probe is positioned in the reactor vessel of the reactor system.

44. The reactor system as recited in claim 43, further comprising a distributor plate in the reactor vessel, wherein the electrical probe is positioned above the distributor plate of the reactor system.

45. The reactor system as recited in claim 44, wherein the electrical probe is positioned above a hole in the distributor plate of the reactor vessel.

46. The reactor system as recited in claim 43, further comprising a distributor plate in the reactor vessel, wherein the electrical probe is positioned between a feedstock inlet and the distributor plate of the reactor system.

47. The reactor system as recited in claim 46, wherein the feedstock consists essentially of a nonpolar material.

48. The reactor system as recited in claim 46, further comprising a recycle line, wherein the feedstock inlet is located in the recycle line.

49. The reactor system as recited in claim 37, further comprising a distributor plate in the reactor vessel, wherein the electrical probe is positioned between a feedstock inlet and a distributor plate of the reactor system.

50. The reactor system as recited in claim 49, wherein the feedstock consists essentially of a nonpolar material.

51. The reactor system as recited in claim 49, further comprising a recycle line, wherein the feedstock inlet is located in the recycle line.

52. The reactor system as recited in claim 37, wherein the electrical probe is positioned in a recycle line of the reactor system.

53. The reactor system as recited in claim 37, wherein monitoring the electrical probe includes monitoring a voltage or current flow between the electrical probe and a ground.

54. The reactor system as recited in claim 53, wherein no external electrical signal is applied to the electrical probe, the voltage or current flow being generated by the electrical probe contacting the bulk material.

55. The reactor system as recited in claim 54, wherein the ground is the reactor vessel of the reactor system.

56. The reactor system as recited in claim 37, wherein monitoring the electrical probe includes detecting a voltage differential between the probe and a ground.

57. The reactor system as recited in claim 56, wherein the ground is the reactor vessel of the reactor system.

* * * * *